United States Patent [19]

Haas

[11] Patent Number: 4,798,214

[45] Date of Patent: Jan. 17, 1989

[54] STIMULATOR FOR EYE TRACKING OCULOMETER

[75] Inventor: Michael W. Haas, Beavercreek, Ohio

[73] Assignee: The United States of America as represented by the Secretary of the Air Force, Washington, D.C.

[21] Appl. No.: 125,633

[22] Filed: Nov. 24, 1987

[51] Int. Cl.⁴ .............................................. A61B 13/00
[52] U.S. Cl. ..................................... 128/745; 351/210
[58] Field of Search ................. 128/745; 351/209–210

[56] References Cited

U.S. PATENT DOCUMENTS

| | | | |
|---|---|---|---|
| 3,036,568 | 5/1962 | Stark | 128/745 X |
| 3,375,375 | 3/1986 | Abbey et al. | 250/216 |
| 3,533,684 | 10/1970 | Stark et al. | 128/745 X |
| 3,551,052 | 12/1970 | Reiber | 128/745 X |
| 3,598,107 | 8/1971 | Ishikawa et al. | 128/745 X |
| 3,777,738 | 12/1973 | Sugita et al. | 128/745 X |
| 4,034,401 | 7/1977 | Mann | 351/210 X |
| 4,109,145 | 8/1978 | Graf | 250/201 |
| 4,304,242 | 12/1981 | Siarkiewicz et al. | 128/745 |
| 4,578,643 | 3/1986 | Junker et al. | 324/202 |
| 4,613,219 | 9/1986 | Vogel | 351/209 |

FOREIGN PATENT DOCUMENTS 8603113 6/1986 European Pat. Off. ............ 351/210

2170910 8/1986 United Kingdom ................ 128/745

OTHER PUBLICATIONS

Young et al., "Survey of Eye Movement Recording Methods"; *Behav. Research Methods and Instrum.;* vol. 7 (5), 1975, pp. 397–429.

Primary Examiner—Kyle L. Howell
Assistant Examiner—Angela D. Sykes
Attorney, Agent, or Firm—Gerald B. Hollins; Donald J. Singer

[57] ABSTRACT

An electronic apparatus for stimulating or actuating an eye sensing oculometer system with simulated eye movement signals that are stable, predetermined, and repeatable. The simulated signals are electrically coupled to an oculometer signal input port in lieu of video signals normally received from an eye viewing camera. Optical images representing infra red reflections from the retina and the cornea portions of the oculometer user's eye are simulated by the apparatus; movement of these images in a computer controlled pattern is contemplated and is emulated by simple operator electable patterns in the disclosed apparatus. The presence of noise signals and eye imperfections are contemplated in the stimulating apparatus.

21 Claims, 7 Drawing Sheets

STIMULATOR FOR EYE TRACKING OCULOMETER

RIGHTS OF THE GOVERNMENT

The invention described herein may be manufactured and used by or for the Government of the United States for all governmental purposes without the payment of any royalty.

BACKGROUND OF THE INVENTION

This invention relates to the field of electronically operated oculometer systems—systems which sense the position and movement of the visual organ or eyeball in a living vertebraed test subject, and more specifically, to apparatus usable as a signal source for stimulating or actuating such oculometer systems.

In many military, medical and machinery control environments, the use of eye movement can be a useful source of command signals for directing the operation of a controlled apparatus. In modern control systems, such ocular responsive arrangements are, in fact, rapidly becoming a technology of choice. In the military environment, for example, the sensing of eye movement of a pilot or an armored vehicle crewmember to accomplish weapon guidance, vehicular steering and other command functions is a currently evolving technology. In other uses of this technology in the medical apparatus field, there is a need for reliable eye movement sensing apparatus to enable severely handicapped patients to communicate with other persons or with life support or living assistance apparatus. Eye movement sensing has also become a useful tool for psychologists and others who study human perception—in the evaluation of reading skills or reading disorders or in the evaluation of TV commercial effectiveness, for example. The use of eye movement sensing for the control of computer or industrial equipment is also now within the realm of technical feasibility.

Although several algorithms for sensing the position and movement of an eye have been proposed, one of the more reliable and technically attractive arrangements for such sensing in at least the case of a human subject is found to reside in the use of selected spectrum energy reflection from the eye. Illumination for this reflection is usually accomplished with a spectral frequency beyond the range of visual response by the eye, and is accompanied by sensing of both the energy reflected from the eye retina and the energy reflected from the eye cornea portion; preferably these two reflections are regarded as being two different signals having a degree of independence.

According to this signal originating arrangement, the infrared reflection from a retina can be expected to appear as a substantially circular optical image while the corneal reflection can be expected to appear also as a somewhat circular optical image residing somewhere within the bounds of the retina reflection image. Such eyeball position sensing systems must, however, be arranged to accommodate a number of real world imperfections or noise source signals, signals which may originate, for example, with the presence of tear fluid in the eye, imperfections or irregularities in the eye components—imperfections such as retina holes or cornea spots, as well as with eyelid closings and dust particles. Oculometer imperfections, such as electronic noise also influence the operation of these sensing systems.

For testing the operation of an oculometer system or the apparatus controlled by an oculometer system, it is often desirable to have a precisely repeatable nonliving organism source of oculometer stimulating signals, signals which can be tailored to resemble a selected input function or to test the limits of the oculometer capability for example. Although signals of this general type could be provided by a human operator by performing a clearly defined routine in a repetitive manner such a human based signal arrangement can be, at once, expensive, unpleasant for the human operator and usually lacking in desired signal precision. Stimulation signals may also be provided by a mechanical apparatus which is arranged to simulate the relevant eye portions and their movement, however, such arrangements are often found to be lacking in desirable flexibility and accuracy. The present invention, therefore, provides a signal sourcing apparatus and method that is capable of overcoming the undesirable features of the heretofore employed signal for an oculometer system.

Oculometer systems per se are known in the patent art; two such systems are described in the patents of Ishikawa, U.S. Pat. No. 3,598,107, and Graf, U.S. Pat. No. 4,109,145. In addition, a device having some of the characteristics of an oculometer but operating on a different principal wherein the movements of a human eye element along multiple intersecting planes are sensed is described in the patent of Abey et al U.S. Pat. No. 3,375,375. An eyesight examination apparatus involving some elements of an oculometer system is also shown in the patent of Siarkiewicz et al. U.S. Pat. No. 4,304,242.

SUMMARY OF THE INVENTION

In the present invention, a combination of electronic circuitry and computer hardware and software is used to generate a video signal which may be used to stimulate or actuate an oculometer system through coupling to a system signal input port. In the described embodiment of the invention, software in the form of an assembly language program is used to determine the nature of the stimulus signal.

An object of the present invention, therefore, is to provide an electronic apparatus capable of generating precisely controlled repeatable signals for stimulating an oculometer system.

Another object of the invention is to provide an oculometer stimulus apparatus wherein the generated output signal is in the form of a video signal having an appropriate mix of video, luminance, and synchronizing information resident therein.

Another object of the invention is to provide a software controllable oculometer stimulating apparatus.

Another object of the invention is to provide an oculometer stimulating apparatus in which either a large variety of stimulus patterns determined by an extensive computer program or a simplified and basic set of patterns determined by an operator manual election, for example, are available.

Another object of the invention is to provide an oculometer stimulating arrangement in which the variability and complexity of the oculometer optical input system can be by-passed to achieve system testing and other precision performance objectives.

Another object of the invention is to provide an oculometer stimulus apparatus which is relatively simple and low in cost.

Another object of the invention is to provide an oculometer stimulus apparatus which may be fabricated from standard and readily available components.

Another object of the invention is to provide an electronic oculometer stimulus apparatus which is free of the failure susceptibility, impreciseness, inflexibility, and other difficulties frequently encountered with mechanical apparatus or with actual human-in-the-loop oculometer operation.

Another object of the invention is to model oculometer response to various "flaws" occurring in human eyes without having to locate a person having these flaws.

Another object of the invention is to provide an oculometer stimulus video signal which can incorporate selected imperfections such as precise noise components, signal timing delays, and nonlinear cornea and retina reflection characteristics.

Another object of the invention is to provide an oculometer stimulus video signal in which the temporal and spatial characteristics of the included eyeball model are controllable.

Another object of the invention is to provide a video model of the human eyeball which may be used in oculometers.

Additional objects and features of the invention will be understood from the following description and the accompanying drawings.

These and other objects of the invention are achieved by signal sourcing apparatus for actuating an eye tracking oculometer system which includes the combination o,f an arrangement for generating first sequence of electrical signals representative of an optical background area, an arrangement for generating a second sequence of electrical signals representative of a first optical image disposed on the background area, an arrangement for generating a third sequence of electrical signals representative of a second optical image disposable on either of the background area and the first optical image, a memory arrangement including a plurality of memory elements, an arrangement for addressing the memory elements, and an arrangement for writing in the memory elements for storing first, second and third sequences of electrical signals, an arrangement for reading the first, second and third sequences of stored electrical signals in predetermined order from the memory elements and for generating a video signal therefrom, and an arrangement for conveying the video signal to a data input port of the oculometer system.

DETAILED DESCRIPTION

Figure 1:
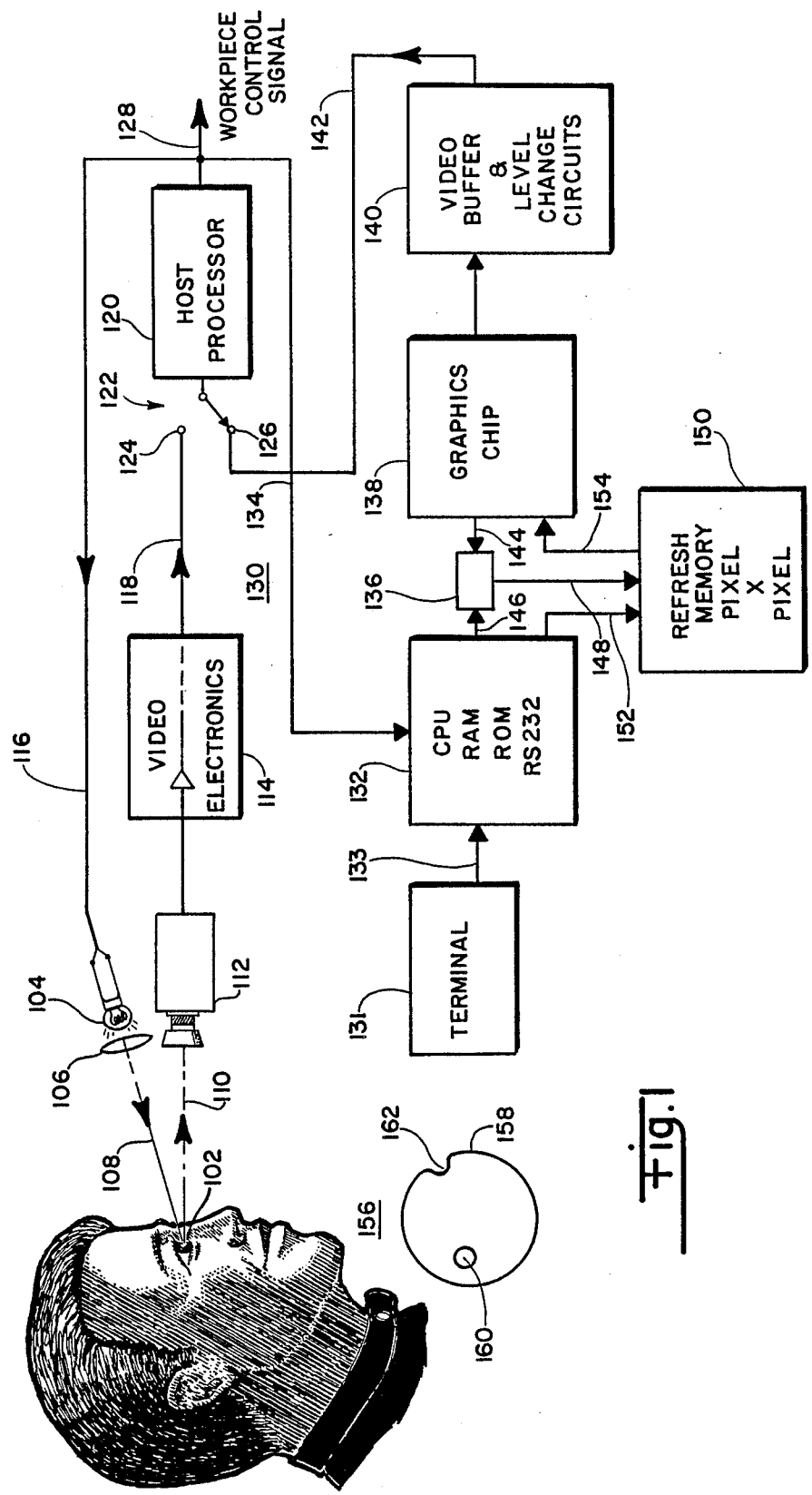
FIG. 1 is a block diagram of an oculometer system arranged for stimulation by either a normal optical signal source or a signal sourcing apparatus of the present invention type.

FIG. 1 in the drawings shows a block diagram of a combination oculometer system and stimulating signal source apparatus for the oculometer system. In the FIG. 1 drawing, an oculometer camera 112 is used to view optical images reflected from the eye 102 of a human subject 100 In the FIG. 1 arrangement, optical energy illumination for the camera observed images originates in a source of optical illumination 104 which may be a source of infrared spectrum illumination such as an incandescent filament or a light emitting diode. This illumination is transmitted through an optical system which preferably includes an infrared filter and a collimating lense arrangement—as is represented by the lens 106. This illumination is communicated to the eye 102 of the human subject 100 along the path 108. The optical image reflected by selected portions of the eye 102 proceeds along the path 110 to the camera 112.

In airborne oculometer systems of the type used by the pilot of a fighter aircraft, for example, the camera 112 is frequently operated in accordance with the 525 line, 30 frame per second N.T.S.C. national television standards used in the United States. The transducer element used in the camera of such a system is frequently comprised of a solid state charge coupled device (CCD) camera of the type recently introduced by Radio Corporation of America/General Electric Company and also manufactured by Fairchild Semiconductor Corporation; other camera transducers such as an image orthocon, and other signal protocols may, of course, be used.

One form in which the image communicated along the path 110 and observed by the camera 112 may appear is shown by the representation 156 in the FIG. 1 drawing. In the representation 156, the infrared reflection typically observed from the retina portion of a human eye is represented by the image at 158 while the reflection from the cornea portion of the eye is represented by the image 160. The cornea image 160 may be located in a number of positions within or outside of the retina reflection image 158 depending upon the position of the human subject's eye at the instant of obtaining the images 158 and 160; that is, movement of the test subject's eye upward, downward, left or right, can be expected to change the relative position of the cornea reflection image 160 with respect to the retina reflection image 158. The interruption of the retina image 158 indicated at 162 is representative of the image "flaws" typically observed in human test subjects.

Since scanning in the camera 112 is not limited to the physical extent of the retina reflection image 158, the retina or pupil image actually appears against a background field which is not shown in FIG. 1, but which is understood to exist. Location of the retina reflection 158 with respect to this background field is, of course, another variable controlled by the test subject eye positioning.

In normal use of the FIG. 1 oculometer system, the low level electrical signal from the camera 112 is conveyed to video electronics circuitry 114 wherein amplification, synchronization pulses and other attributes of a video signal are added. The video signal is transmitted along the path 118 to the host processor 120—assuming the switch 122 is in the closed position for contact 124. In the host processor 120 analysis of the video signals representing the image of the type shown at 156 in FIG. 1 is accomplished and a command or workpiece control signal indicating eye position is generated for transmission along the path 128. The workpiece control signal may, in the airborne oculometer system, be used for directing weapons such as guided missiles or for aircraft flight control or other purposes. The path 116 in FIG. 1 provides for the feedback or closed loop controlling of the optical illumination source 104 by the scanned optical image. By way of this feedback path, optimum intensity for the illumination source 104 is obtained.

Additional details of an oculometer system of the type described thus far are to be found in the patents of Graf and Ishikawa U.S. Pat. Nos. 4,109,145 and 3,598,107, which were referred to above, and also in the references identified in these patents.

During the design, adjustment, testing, or maintenance of an oculometer system of the type described or of the equipment connected to such an oculometer it is often desirable as is referred to above to have available a predetermined repeatable—a signal stable signal for test or stimulation use and in lieu of the signal transmitted along the path 110 in FIG. 1 Although apparatus capable of generating an image of the type shown at 156, could conceivably use the camera 112, in combination with some mechanical or electro-mechanical apparatus, it is found convenient in many instances to generate these artificial stimulus signals by way of electronic techniques and to then substitute these stimulus signals for the video signal communicated along the path 118 in FIG. 1—especially since such an electronic signal is more easily controlled and manipulated.

The apparatus shown at 130 in the lower portion of FIG. 1 is capable of generating such predetermined, stable, video signals for use in the host processor 120. The switch 122, of course, provides a convenient arrangement for electing between the predetermined signal source 130 and the normal eye originated signals arriving via the path 142 and the switch contact 126.

The predetermined stimulus signal source apparatus 130 includes generally a pixel by pixel organized memory 150 in which signals representing images of the type shown at 156 and the background area surrounding these images are to be stored. The stored optical image representative signals are generated in a microprocessor central processing unit which includes appended ROM and RAM and other circuits, all of which are indicated by the block 132. The stored signals are communicated along the path 152 and their addressing information communicated along the path 148 between the block 132 and the memory of block 150 The selection of image position, and shape, image movement velocity, and other characteristics such as noise, of the optical image stored in the memory 150 is accomplished by signals originating in a computer terminal 131 and communicated along the path 133 to the central processing unit of block 132.

Once an optical image of the type shown at 156 in FIG. 1 has been stored in the memory 150, accessing of this image for use in the host processor 120 is accomplished by way of a graphic chip circuit represented by the block 138 in FIG. 1; the accessed information is further processed as to signal format in the video buffer and level change circuitry of block 140. Signals representing the stored optical image are communicated from the memory 150 to the graphics chip 138 along the path 154. According to the preferred arrangement of the present invention, variations in the information written into the memory 150 rather than variations in the readout sequence are used to control the apparent position and velocity of the image presented to the host processor along the path 142. Such variations may, of course, be accomplished by changes in the data pattern and the addressing pattern for the information stored in the memory 150 at the time of its storage.

The separate paths for writing and reading of the memory 150, that is the paths 152 and 154, imply some form of timesharing of the memory read and write operations; in such memory arrangements a segregation of the reading and writing addresses conveyed to the memory is also required in order that simultaneous memory writing and reading events at a single memory location be avoided. In the FIG. 1 apparatus, the circuitry of block 136, which receives address information from both of the paths 144 and 146, is used to segregate the memory reading and writing operations. A feedback signal path 134 is used in the FIG. 1 apparatus to provide control of the microprocessor's central processing unit, block 132, in response to the workpiece control signal output 128; this feedback path can provide generated eye position information to the CPU, or information concerning noise levels, pupil and cornea shape, or other automated command information. Commands to the CPU can also be entered through the terminal.

Figure 2:
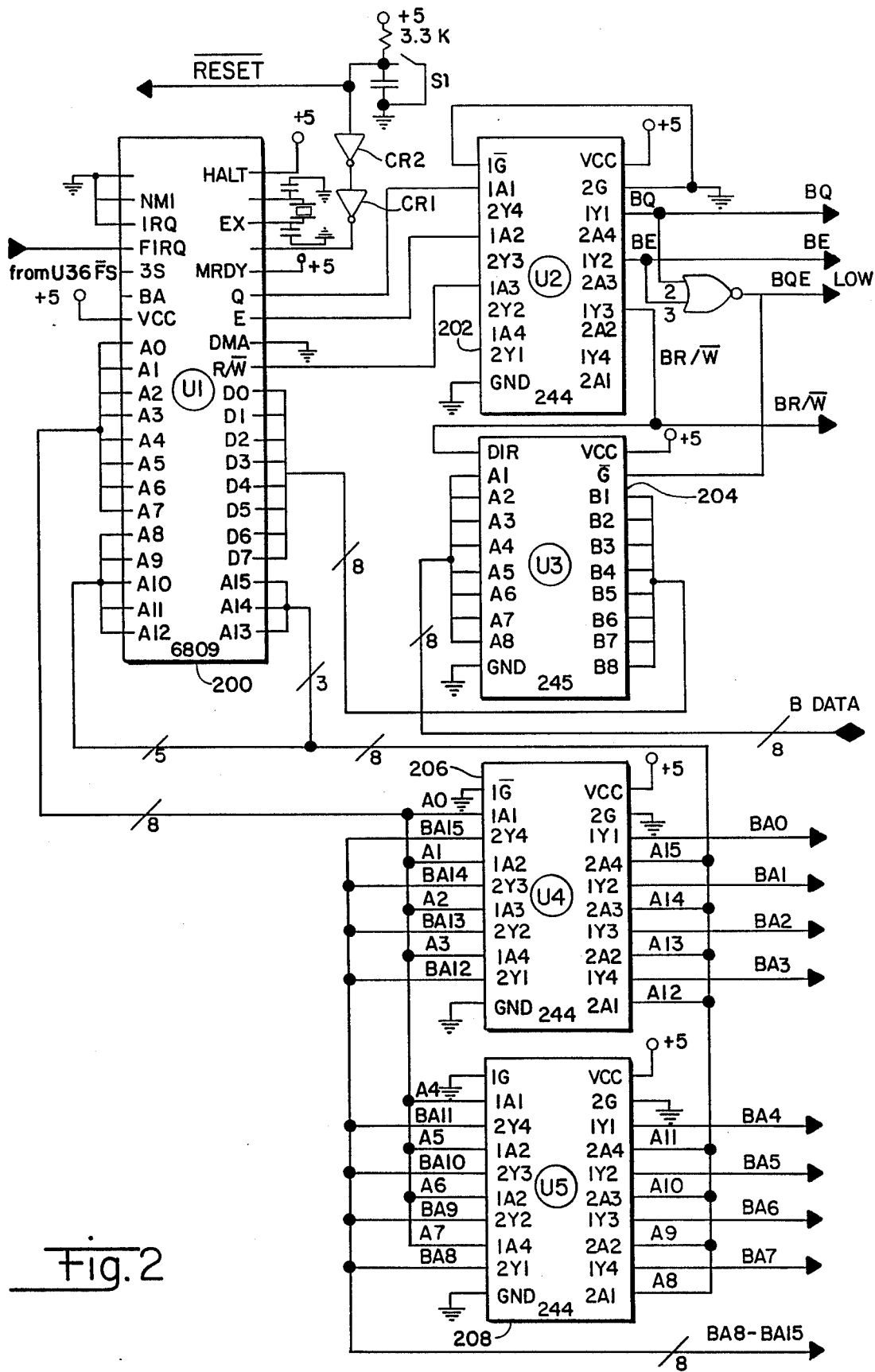
FIG. 2 is a block diagram of a portion, including a microprocessor of an oculometer signal sourcing or stimulating apparatus arranged according to the present invention.

Additional details of the electronic circuitry used in embodying the predetermined stimulus signal source apparatus 130 in FIG. 1 are presented in FIGS. 2–6 of the drawings herein. Information regarding the computer program used with the central processing unit of block 132 in FIG. 1 is also included in appendix A herein. In the following description of this circuitry and program, the circuit elements appearing in FIG. 2 are numbered in the 200 series, the elements in FIG. 3 with the 300 series, an so on. Where appropriate, numbers used in a previous figure are repeated in a later figure without change, that is, a given element maintains the sam identifying number throughout the circuit and software description. The element identifying numbers are shown external to the blocks in the FIG. 2 diagram; the numbers inside the blocks in the diagram identify the type of integrated circuit chip being used and the number and letter combinations inside the block identify the circuit chip pin numbers.

FIG. 2 of the drawings shows at 200 the microprocessor used in the FIG. 1 stimulus signal source apparatus 130 together with buffer circuits, 202, 204, 206 and 208, used for coupling the microprocessor signal to other portions of the electronic circuitry. The buffering circuits at 202 and 204 in FIG. 2 provide driving capabilities for the read, write and other control signals and for the data lines of the microprocessor respectively. The buffering circuits 206 and 208 provide drive capability for the address lines of the microprocessor. As indicated by the numbers located within the FIG. 2 blocks, microprocessor 200 may be a Motorola type 6809 and the buffering circuits 202, 204, 206, an 208 may be type 244, 245, 244 and 244 integrated circuit devices respectively. The type 6809 microprocessor is available from Motorola, Inc., while the type 244 and 245 buffer circuits are available from Motorola, National Semiconductor and other commercial manufacturers using the complete designations 74LS244 and 74LS245.

Figure 3:
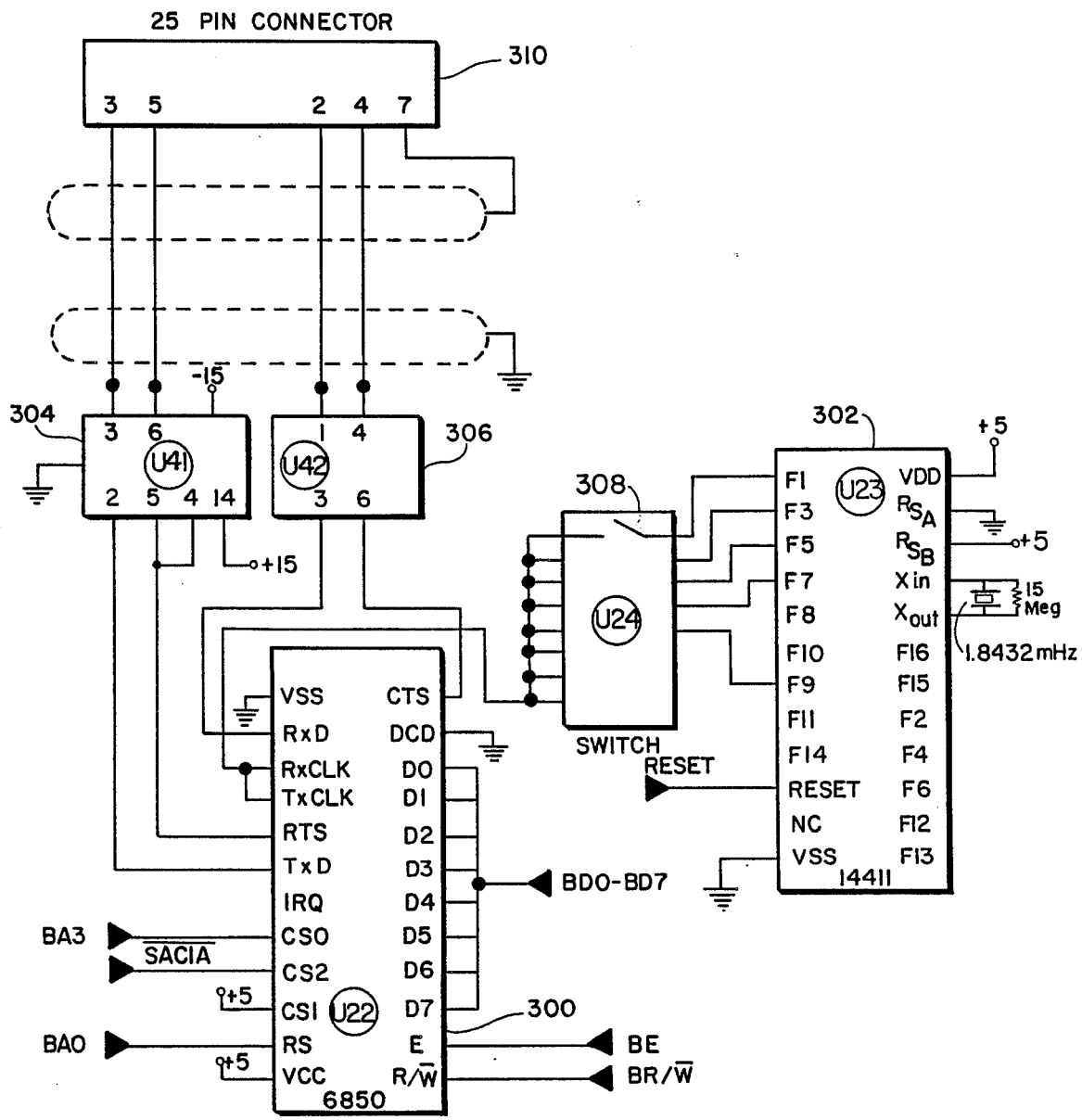
FIG. 3 is a block diagram of a communications port usable with the oculometer stimulation apparatus of the present invention.

In the FIG. 3 portion of the stimulus signal generating apparatus is shown the circuitry for an RS 232 communications interface which enables communication between an external computer or terminal and the microprocessor 200. Communication of this type is useful for the purpose of de-bugging the microprocessor program as is explained in the appendix in connection with the employed monitor routine. The communication interface of FIG. 3 includes a Motorola type 6850 communications chip and a type 14411 chip which is used for clock generation and rate selection for the communications interface. Signals communicating with the computer terminal pass through the buffer circuits 304 and 306 and the usual 25 pin connector shown at 310 in FIG. 3. The RS 232 port at the connector 310 supports communication to the terminal which is used for initial boot-up when the monitor program is included in the software load. The terminal is used by the monitor program to look at memory, set memory, set break points in the application program, and begin execution of the application program.

Figure 4:
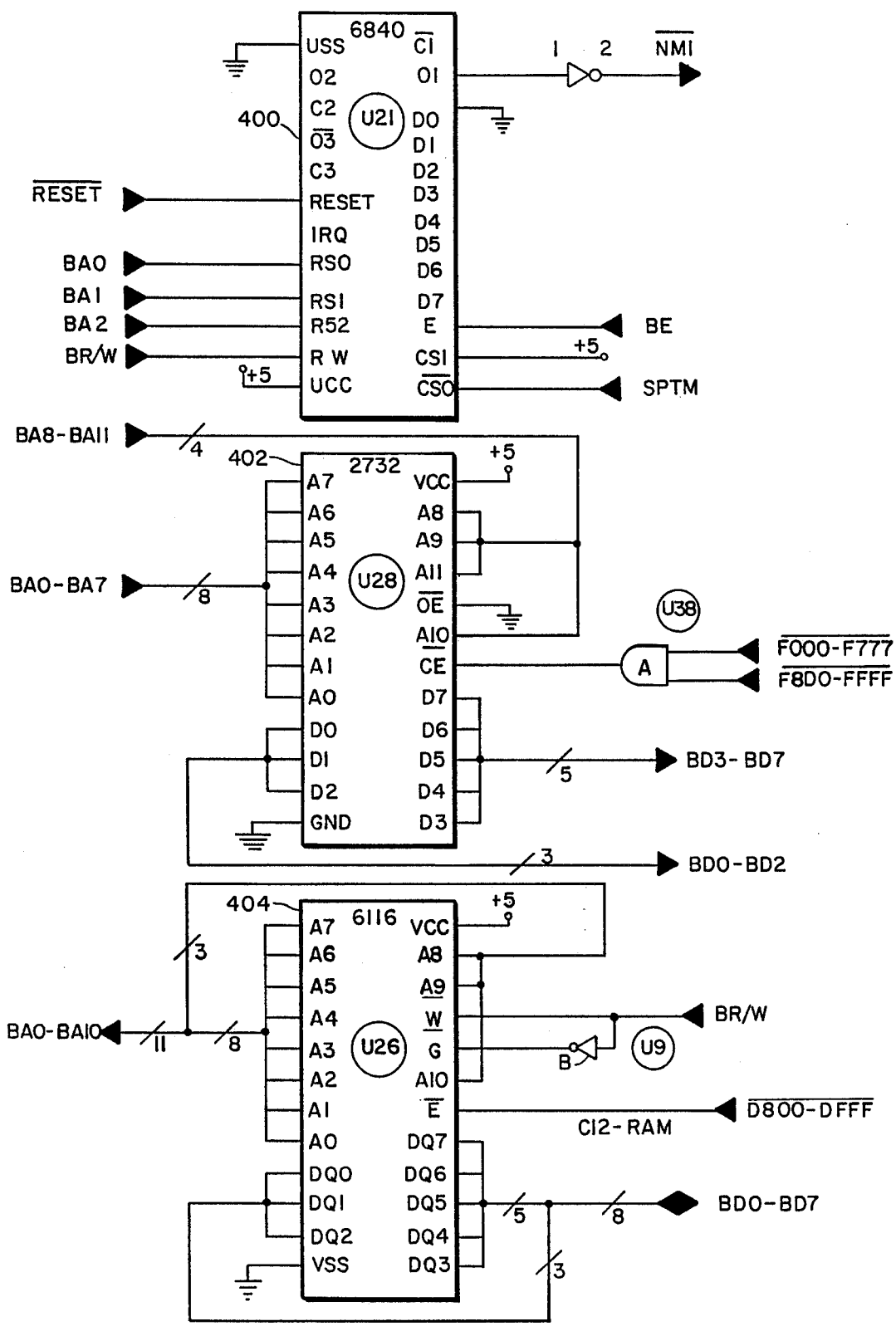
FIG 4 is a block diagram of a timer, ROM, and RAM circuit elements usable with the oculometer stimulation apparatus of the present invention.

FIG. 4 of the drawings shows at 402 and 404, the read only memory (ROM) and random access memory (RAM) circuits associated with the central processing microcomputer chip 200 of FIG. 2 along with a programmable timer circuit 400 which may be employed to periodically interrupt the microprocessor 200 to update the optical images generated. This interrupt may be arranged to occur at some predetermined time interval such as every 15 milliseconds if the program residing in the microprocessor is of such running time length as to require an interrupt function. In the exemplary microprocessor program described below, the graphics chip provides interrupts and precludes a need for use of the timer chip 400.

The circuit 402 is preferably a UV ROM chip and holds the application program and monitor program it uses. It resides at addresses F000 hex to FFFF hex. Chip 404 is a RAM chip which communicates only with the CPU and is used for CPU variables It resides at addresses D800 hex to DFFF hex.

Figure 5:
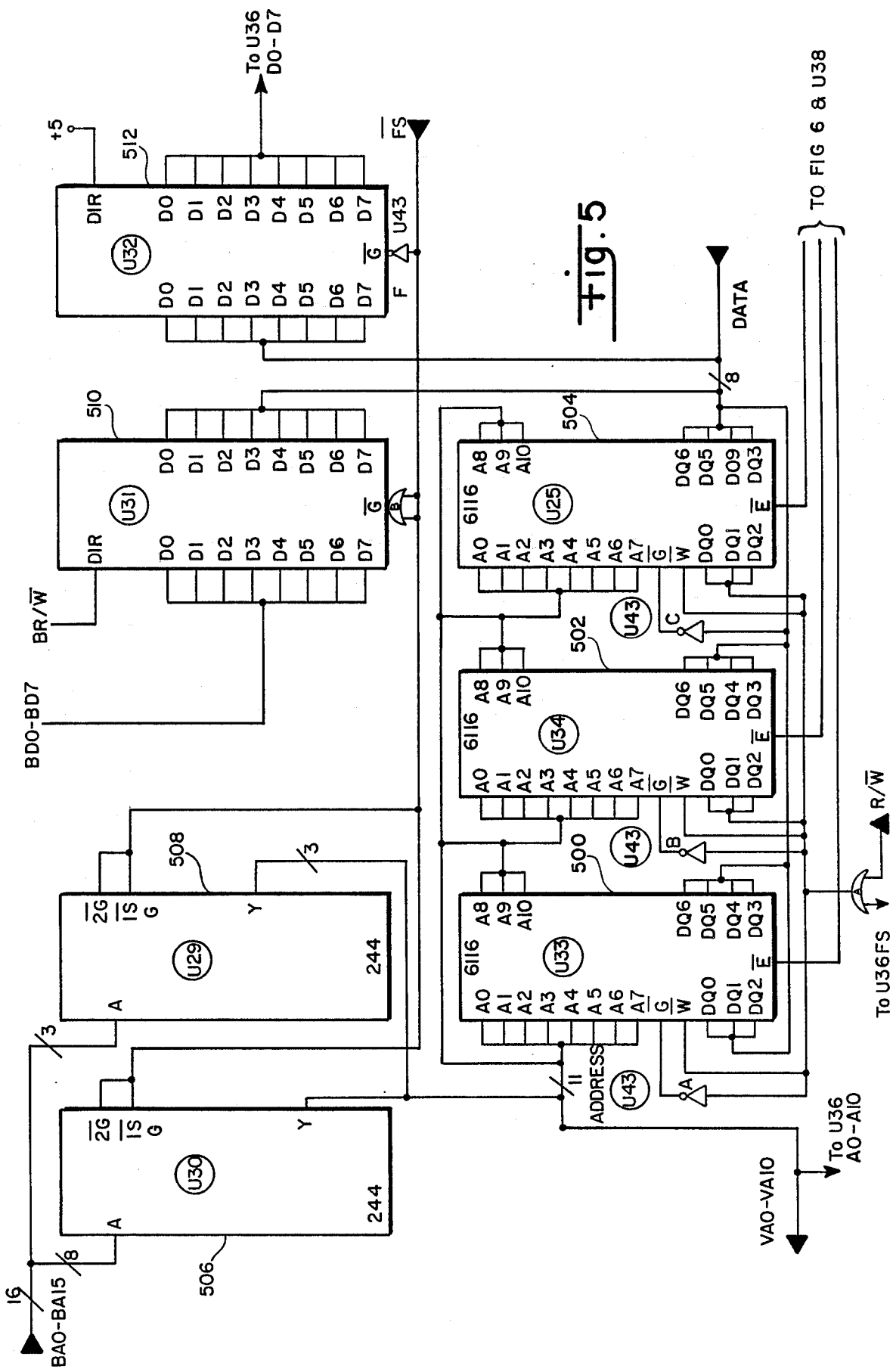
FIG. 5 is a block diagram of a pixel by pixel organized memory usable with an oculometer stimulating apparatus according to the present invention.

The pixel by pixel organized refreshed memory shown at 150 in FIG. 1 is comprised of three Motorola type MC6116 memory circuit chips shown at 500, 502 and 504 in FIG. 5 of the drawings, together with the Tri-State address buffer circuit chips 506 and 508 and the data buffer circuit chips shown at 510 and 512 The MC6116 chips provide 16 k bits of memory per chip.

Figure 6:
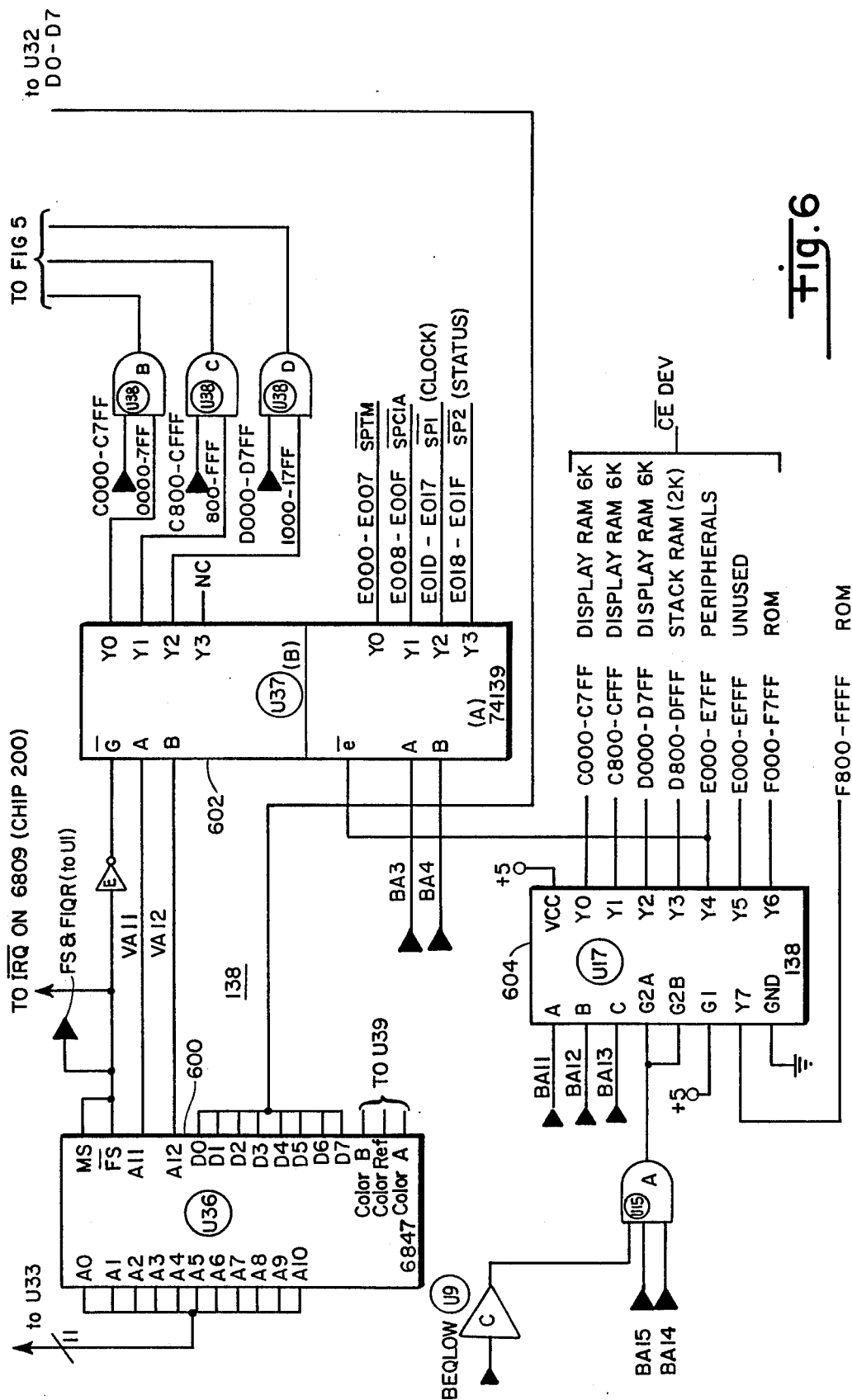
FIG. 6 is a block diagram of a graphics control chip and associated circuitry usable in an oculometer stimulation apparatus according to the present invention.

The graphics chip, a Motorola type 6847 circuit, is shown at 600 in FIG. 6, along with an address decoding circuit 602 and a type 138 bus access controlling circuit at 604. The 6847 circuit pulls the pixel data out of memory and assigns color or luminance value to each pixel as it generates the video signal. The operating mode of the 6847 circuit is controlled by external signal lines of the 6847 circuit; this mode determines the pixel format.

The bus access control circuit 604 determines which of the competing circuits, that is the microprocessor 200 and the graphics circuit 600, has access to the refresh circuits 500, 502, and 504 at any instant of operating time. The access control circuit 604 also precludes double or simultaneous accessing of the memory by both the microprocessor circuit and the graphics processor circuit. The bus access control operates by allowing the 6847 circuit to arbitrate use of the address and data lines. The 6847 circuit will seize the address lines when it has need therefor; when the 6847 circuit does not need the address lines, however, it goes into a high impedence state allowing their use by the CPU. The 6847 circuit also arbitrates use of the data lines but uses external circuitry to do this; this circuitry resides in the buffer circuit chips 510 and 512.

The $\overline{FS}$ (or /field sync) line is the key allowing CPU access to the pixel memory. The 6847 circuit uses the $\overline{FS}$ line to indicate its utilization of the memory. Buffer chips for address and data line arbitration are connected to the $\overline{FS}$ line for use as a chip select signal. When the 6847 circuit wants the memory, it drives the $\overline{FS}$ line high and does not select the CPU buffer chips, 506, 508, 510. When the 6847 circuit releases the memory, the $\overline{FS}$ line is pulled low, the buffer circuit chip 512 is selected and this selection connects the 6847 circuit data lines to the pixel memory. The $\overline{FS}$ line is also tied to the 6847 for interrupt and software syncronization.

Figure 7:
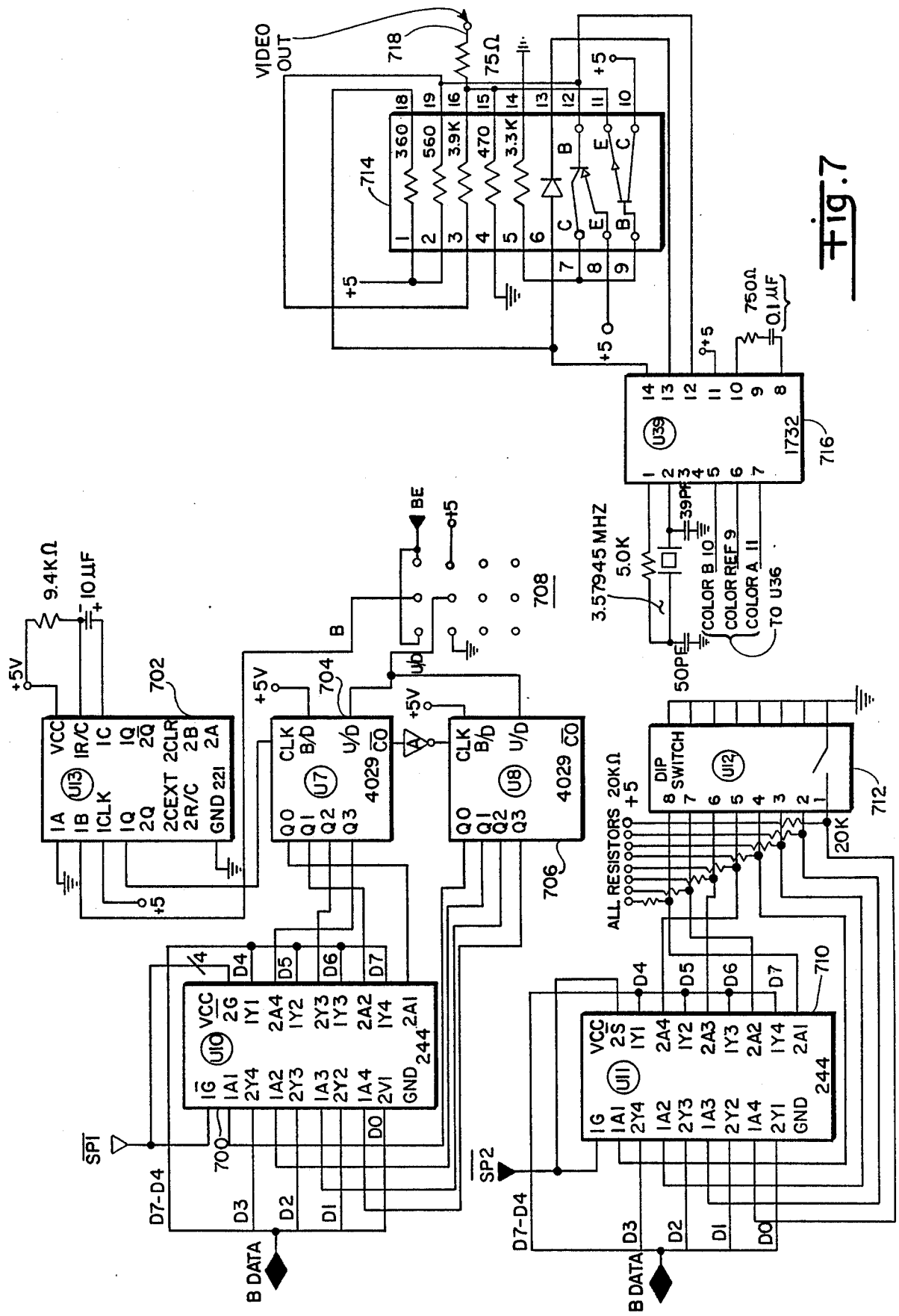
FIG. 7 is a block diagram of a control signal input and output signal buffer arrangements usable with the oculometer stimulus apparatus according to the present invention.

FIG. 7 of the drawings shows three peripheral circuits used with the oculometer stimulus apparatus of FIGS. 1-6 to enable human election inputs to the apparatus and for output signal processing. In other embodiments of the invention, these circuits can be replaced with a parallel input from a host computer. At 700, 702, 704, 706 and 708 in FIG. 7, are shown the elements of a circuit array used to enable operator selection of the present embodiment provided simple cornea and retina movement patterns. The election of a right moving, left moving or stationary cornea reflection image is made in the FIG. 7 circuitry according to disposition of the three position switch 708 in the left, right o center positions. A right hand positioning of the switch 708, for example, connects the U/D terminal of the counter circuit chip 70 to a +5 volt supply while a center most position of the switch 70 causes this terminal to be in an open condition. The counter of circuit chip 704, of course, counts in the upward progressing or downward progressing direction depending upon the positioning of the switch 708. The circuit 702 in FIG. 7 is a type 74221 circuit chip used as a clock generator for the up-down counter.

The switch 712 and the switch buffering circuit 710 provide simplified and exemplary mode control arrangement in lieu of the host processor 120 in FIG. 1 and thereby allows operator selection of a "generate cornea," "generate pupil". and other possible operating modes for the stimulus apparatus. Current from the 20 kiloohm resistors connected to the input terminals of the circuit 710 drives all except the one or more switch closed inputs of the circuit 710 to be in the active condition in order to elect the desired operating mode for the stimulus apparatus. The circuit 710 serves as a buffer for the data lines and is selected by address decoding. The switch 708 is shown in FIG. 7 as a simplification over the use of a host processor: other embodiments of the invention can, of course, employ the desirable capabilities of a host processor. The parallel port can be used by removing the switch and putting in input lines from the parallel port of such a host processor.

The Motorola type 1732 translator chip at 716 in FIG. 7 serves to generate, from the color and reference signals outputs of the graphics processor chip 600 in FIG. 6, a composite video signal which includes synchronization pulses. Timing of the synchronization pulses provided by the translator chip is determined by the 3.57945 megahertz quartz crystal shown connected to pin 2 of the translator chip; a crystal of this operating frequency provides scanning times desired in a 525 line composite video signal.

The network shown in the circuit 714 in FIG. 7 provides buffering amplification for the composite video signal output of the stimulator. The buffer amplifier shown in FIG. 7 is a common emitter - emitter follower feed-back pair with a DC feedback path. a 3.9 K resistor, connected between pins 3 and 16 of the DIP socket used for mounting the network of block 714-or between the output emitter and the input base nodes. A circuit of this type is described at page 3-480 of the handbook DL-133 published by Motorola Incorporated and is otherwise well known in the art. The video output signal at 718 in FIG. 7 is compatible with the output signal from the camera 112 and the video electronics 114 in FIG. 1 and can, therefore, be connected to the terminal 26 of the switch 122 in FIG. 1 and to the input of the processor 120.

Software

Appendix 1 herein comprises an assembly language listing of a routine that is suitable for use in the microprocessor central processing unit 200 for generating simulated FIG. 1 type retina and cornea images. The operation of this program is believed comprehensible from the substance of the program listing to persons skilled in the electronic and computer arts, especially in view of the notes and comments included in the program listing. Additional explanatory material is nevertheless included herein to assure optimum understanding of the program and its relation to the disclosed hardware of the invention and in respect of the standards for patent disclosure in such systems.

Turning now to the program listing, the steps beginning with the IFEQ instructions on the page I set up locations for the interrupt vectors for reset and frame synchronization events in the stimulus apparatus. The group of instructions commencing with the ORG instruction and ending with the ENDC instruction accomplish initialization of program variables.

Returning momentarily to page I of the program listing, as indicated by the first two lines of assembly language code, the software used with the FIGS. 1-7 apparatus may electively employ the assistance of a monitor software routine such as the Motorola ASSIST 09 *Realtime Monitor* for debugging and system startup. Use of such monitor software is invoked by the illustrated software code wherein the second MNTRLD macro instruction, MNTRLD=1, executes in lieu of the first MNTRLD=0 macro instruction which is excluded from execution by the preceding asterisk in the listing shown. Depending upon the value of the variable MNTRLD which is assigned in the first two lines of code, one of the IFEQ or IFNE MNTRLD sequences at the bottom of the first page or at the top of the second page of the appendix will execute. Execution of the IFNE MMTRLD code tells the monitor software to set up the address IRQRTN as the interrupt vector for the interrupt code FFF8, thereby assigning control of the interrupt signal when it occurs to the instant program rather than to the monitor software The group of instructions commencing with the BEGIN statement on the second page of the appendix listing serve to clear the program variables from previous execution attained values or from computer power-up attained values. These clearing operations are performed by the CLR instruction in the case of 8 bit variables or in the case of a 16 bit variable, by loading the D register with 16 bits of zero using an LDD instruction followed by storing in the variable such as the variables POFF and COFF, the zero-information. In the convention of the appendix software, the # symbol, indicates a literal number while the $ symbol, indicates a number to the hexagon base. The ORCC instruction in this clearing sequence sets the IRQ and FIRQ masks in the 6809 processor to temporarily preclude the recognition of interrupt signals from the display processor. The prototype software was also run without syncronization Some flickering of the video was thereby apparent as the image changed.

The clear display sequence commencing at the middle of appendix page II serves to fill the refresh memory, that is the memory 150 in FIG. 1 and the memory circuit 500, 502, and 504 in FIG. 5, with an all black background image - an image comprised of all logic 1 values. This background field information is accomplished by loading a value of all 1's into the Y register of the microprocessor and then looping between the first and last addresses in the memory - after receiving a synchronizing pulse from the 6847 graphics chip 600 in FIG. 6 and 138 in FIG 1. By way of delay until a graphics chip synchronizing signal is issued, the graphics chip is accorded primary access to the memory of blocks 150 500, 502 and 504 and the microprocessor is accorded a secondary or slave accessing status to the memory. The graphics chip releases its access to the memory by an active signal issued on the FS line. Each storing of data retained in the Y register, all 1's, occurs in two successive addresses followed by an incrementing by two addresses as indicated by the X+ + instruction. Storing continues in a loop until the last X value has been attained.

The MLOOP sequence just below the middle of appendix page II, reads the status switches of block 712 in FIG. 7 by Way of the equate commands and the E018 values assigned to the PIOCMD variable in the third and fourth lines of code on page one of the appendix listing. The switches of block 712 may, of course, be replaced by a buffer register when computer selection of pupil and cornea movement patterns in a complex test sequence is desired. The switches of block 712, therefore, represent a simplified, essential principles representation of such a computer patterns sequence arrangement. The MLOOP sequence executes indefinitely until a predetermined condition of switches 1 and 8 in block 712 is sensed - this arrangement allows the image read to the memory of blocks 500–504 to remain stationary and meaningful during changes of the switches in block 712 to select a different movement pattern for the retina and cornea images.

Commencing with the LDB command at the bottom of appendix page II are four groups of instructions which determine image positions - the pupil or retina image X position, the cornea image X position, the pupil or retina image Y position and the cornea image Y position respectively. These instruction groups may be identified as test1, test2, test3, and test4 respectively; labels for the test2–test4 sequences are provided in the listing, however, the test1 label is omitted. Each of these code sequences makes use of the sub-routine XOFFST, which is shown on page VI of the appendix, in order to increment the respective X or Y position of the image under consideration. Selections between the test1–test4 sequences is made according to the value of the variable PIOCMD which is loaded into the B register and compared with the test enabling variables CMDPPX, CMDCRX, CMDPPY, and CMDCRY respectively, the compared value originate in the mode switch 712 in FIG. 7. Changes made to the magnitude of the pupil horizontal or X offset variable through use of the subroutine X offset cause left and right movement of the retina while changes in the pupil vertical or Y offset variable PUPYOF cause up and down movement of the retina and similarly changes in the variables CORXOF and CORYOF cause X and Y direction movements of the cornea image.

By way of explanation, the variable names, labels, and notes used in the appendix program listing employ the term "pupil" rather than the term "retina" that has been used herein before; these two terms refer to the same optical image, an image resulting from light transmitted through the pupil to the retina and back through the pupil of the user subject's eye.

The left or right, up or down movement of a generated image is determined by the switch 708 in FIG. 7, the movement rate is determined by the 9400 ohm resistor and ten microfarad capacitor combination appended to the block 702 circuit in FIG. 7.

At the label test5 on page II of the appendix software listing is a code sequence which generates a series of test image bars for diagnosing or appraising performance of the FIGS. 1-7 apparatus. Following the test5 sequence, the code commencing with the label TLOOP comprises a series of three nested loops wherein the contents of the B register is repeatedly written into the display or refresh memory of blocks 138, 500, 502 and 504 and this B register content is varied between light and dark conditions in a regular pattern which allows visual diagnosis of memory problems other apparatus and software problems in the FIGS. 1-7 apparatus.

Upon completion of any of the test1-test5 sequences, a jump to the code at the label DWRITE, located at the top of page IV of the appendix program listing, occurs. In the DWRITE code, the memory contents representing pupil and cornea optical images are transferred in pixel by pixel sequence from the memory to the oculometer system under stimulation. The initial steps of the DWRITE code achieved storage of the 16 bit words representing old pointers for the pupil and cornea offset quantities in order that the signals at these locations, the signals representing the old pupil or retina image and the old cornea image, may be later erased or replaced with background level intensity information. Storage of the old pointers is accomplished in the first four steps of the DWRITE sequence by way of transferring through the D register into the variables OPOFF and OCOFF the old pointer information.

Computation of a new pupil offset value is accomplished by the DWRITE code sequence between the LDD COFF instruction near the top of appendix page IV and STD POFF instruction near the middle of page IV. The function implemented during this computation is the X+(Y*ROWSIX) mathematical function that is indicated in the comments following the instructions. A branch instruction, BRA and the label "switch" are used to accommodate possible negative values of the pupil Y offset value. A finally computed value of pupil offset is transferred from the D register to storage in the variable POFF in the code line identified with the label STRIT. The D register in the DWRITE sequence is simply the A and B registers concatenated (A:B). Generally in the DWRITE sequence, the old values for POFF and COFF are first stored using the D register, then the A register is loaded with pupil X offset value.

The computation of cornea offset value follows the pupil offset computation and commences just below the middle of page IV of the appendix; this computation is similar to the described computation for pupil offset with the exception of different label and variable names as are appropriate.

Commencing at the top of page V in the program listing are two loop routines by which the pixels of an old pupil image and an old cornea image are erased or returned to the background black, logic one, status in the display or refresh memory. In these routines addresses for the pupil image pixel elements are accessed in the pixel element address array shown on pages VII and VIII of the appendix and to each array address in turn is added the above stored old pupil or cornea offset value, OPOFF or OCOFF - in order to access and clear out each element of the old image. The starting address for the accessing and clearing operation is determined by the PUPPTN label which also appears in the page VII array while the loop which performs the addition and erasing o pixel intensity is identified with the WLOOP1 label. The adding of array and offset values occurs in the ADD instruction and the erasing of the memory pixel to an all 1 status occurs after receipt of a synchronizing pulse from the LDDFFF and STD,Y instructions within the WLOOP1 sequence. The variable PUPSIZ determines the size of the pattern of the pupil. The value of the variable TABEND is computed by using the start address and adding the size. This allows variable pupil and common patterns in accord with RAM contents. Generally in the WLOOP1 sequence, X is used as the address of the pattern being written. Once X gets large enough to be at the end of the table (TABEND), writing stops. The CMPX instruction is a subtraction operation. The accessing of another address, comparison with ending address, and branching for another pixel, processing steps follow the clear of one pixel instruction in the WLOOP1 sequence.

The accessing and clearing of the cornea image pixels is accomplished in a similar manner commencing with the LDD #CORPTN instruction and the WLOOP2 sequence. Upon completion of the WLOOP1 and WLOOP2 sequences, the memory is once again in a fully erased or backgrounded status containing all logical one values.

The WLOOP3 and WLOOP4 sequences on pages V and VI of the appendix are similar to the above described WLOOP1 and WLOOP2 sequences except that intensity values other than the all black or all logical one value are being loaded into the memory and, of course, this data is loaded into memory locations representing a new pair of optical images. In the WLOOP3 sequence, the POFF variable following the WLOOP3 label line, represents the offset value for the new pupil image location in memory.

The physical extent of the pupil and cornea image sizes is determined by the variables PUPSIZ and CORSIZ which are entered on page VIII in the appendix program listing. The intensity of the image representing the pupil and cornea images is determined by the even numbered line entries in the cornea pattern and pupil pattern address arrays, that is, by the numeric values $5555 in the case of the cornea array and the value $0000 in the case of the pupil array. These numeric values represent a gray level intensity and the brightest white level intensity respectively so that the image presented to the oculometer apparatus represents a black background on which is superimposed a gray level pupil image and on which is received a bright white cornea. Other intensity values, image shapes and image sizes can, of course, be readily provided by the invention. The odd numbered lines in the cornea and pupil arrays represent address vectors.

Upon completion of the WLOOP4 sequence, the program calls for a return to the MLOOP label in the "clear display" sequence on page II; that is, the microprocessor is cause to enter a looping sequence wherein signals are repeatedly furnished to the oculometer system under test. As indicated by the "hopefully 2.03 milisecond" comment following the WLOOP4 sequence on page the graphics processing chip is arranged to preempt other accessing of the memory at time intervals of 2.03 milliseconds: it is, therefore, desirable for the described processor sequence to execute in less than 2.03 milliseconds. The SYNC instructions, which are disposed throughout the program additionally cause the microprocessor to be subservient to the graphics processor chip with respect to memory accessing. The program will, however, operate without the SYNC instructions and in some cases, the SYNC instructions merely slow the response of the software.

Below the MLOOP return instruction on page VI of the program listing are two messages which may be used in conjunction with the monitor software to aid in program debugging. The IRQRTN instruction following the messages is used in connection with the sync instructions which have been described above - the microprocessor jumps to the IRQRTN label upon receipt of any of the recited sync pulses. The IRQRTN label leads the microprossor to the RTI instruction which causes a return to the point of departure executed just prior to the sync command.

At the lower portion of page VIII of the program listing, a number of variables used heretofore in the program are defined. The CMD sequence of variables in the page VIII listing are used in conjunction with the switches of the block 712 for selecting generated image parameters.

On page IX of the appendix program listing are recited the constants which are stored in the ram chip 404 in FIG. 4, the addressing of these RAM constants commencing with the address D800 as listed at the top of page IX. The software described above is, of course, stored in the ROM chip 402 in FIG. 4 of the drawings. The RAM constant listing at the top of page IX allocates addresses in the RAM used by the program.

The present invention therefore provides a reliable, stable, and low-cost arrangement for actuating an airborne or other oculometer system in a manner which is advantageous for testing, diagnostic and other non-user oriented applications of the sytem. The disclosed apparatus is especially useful and flexible in comparison with the mechanically based oculometer stimulus devices which have been heretofore used and is also enhanced by the use of electrical signal rather than optical signal coupling into the oculometer system. The disclosed system is particularly advantageous with respect to using human based signal sources which are not as precise or may not exhibit the characteristics desired for testing.

While the apparatus and method herein described constitute a preferred embodiment of the invention, it is to be understood that the invention is not limited to this precise form of apparatus or method and that changes may be made therein without departing from the scope of the invention which is defined in the appended claims.

```
        OPT   ,L
        NAM  ETESIM
*
******** AUTHOR:     MR. MICHAEL HAAS
*
*
*
*MNTRLD         EQU 0      ZERO MEANS NO MONITOR TO LOAD
MNTRLD          EQU 1      ONE MEANS MONITOR WILL BE LOADED
*
*      THIS ROUTINE DRIVES THE 6809 SYSTEM
*      BUILT FOR THE ELECTRONIC EYE-TRACKER STIMULATOR.
*      IT WAS WRITTEN IN THE SPRING OF 1985 AND CONTAINS
*      TWO FUNCTIONAL BLOCKS.
*      THE FIRST BLOCK IS THE MAINLINE ROUTINE.
*      THIS ROUTINE POLLS THE SIMULATED PARALLEL
*      PORT TO DETERMINE IF A VALID COMMAND IS THERE.
*      IF THERE IS, IT DETERMINES WHAT TO DO ABOUT IT.
*      THE MAIN OUTINE SETS UP THE MEMORY FOR THE SECOND
*      OUTINE TO PEFORM IT'S FUNCTION WHEN CALLED IN A
*      EFFICIENT FASHION.
*      THE SECOND BLOCK IS INVOLKED
*      EACH FRAME SYNC OF THE VIDEO SIGNAL. DUING THIS TIME,
*      THIS ROUTINE HAS ABOUT 2.03 MS TO WRITE TO THE DISPLAY
*      RAM. INITIALLY, IT CHECKS FLAGS WHICH ARE SET BY THE MAINLINE
*      TO INDICATE WHAT FUNCTION TO PERFORM, AND THEN DOES THEM.
```

```
*****   NOTE::  THE DISPLAY WRITE ROUTINE DOES NOT KNOW WHEN THE 2.03 MS
  *     HAS EXPIRED.
  *
 **
  *
  *
  *     SET UP EQUATES FOR THE REST OF THE ASSEMBLY
  *
PIOCNT          EQU $E010
PIOCMD          EQU $E018
  *
  *
  *     SET UP THE INTERUPT VECTORS FOR RESET AND FRAME SYNC
  *
        IFEQ MNTRLD
        ORG $FFF8       REGULAR VECTOR IRQ
        FDB IRQRTN
        ORG $FFFE
        FDB BEGIN
  *
        ENDC
  *
  *
  *
        ORG $F000
  *
IRQRTN  LEAX IRQRTN,PCR
        LDA #12
        SWI
        FCB 9
        RTS
        ENDC
  *
  *     BEGIN MAINLINE ROUTINE
  *
BEGIN   ORCC #$40
        LDD #$0000
        STD POFF
        STD COFF
        CLR OLDPX
        CLR OLDPY
        CLR OLDCX
        CLR OLDCY
        CLR PUPYOF
        CLR PUPXOF
        CLR CORXOF
        CLR CORYOF
  *
  *
*****   CLEAR DISPLAY
  *
  *
        LDY #$FFFF
TOP1    LDX #$C000
CLOOP   SYNC
        STY ,X++
        CMPX #$D7FF
        BMI CLOOP
```

```
MLOOP LDB PIOCMD
      BPL MLOOP
*
*
**      FELL THROUGH BY VALID COMMAND
*
*
*
*
*
*
      LDB PIOCMD
      CMPB CMDPPX
      BNE TEST2
      JSR XOFFST
      STA PUPXOF
      JMP DWRITE
*
*
TEST3 CMPB CMDPPY
      BNE TEST4
      JSR XOFFST
      STA PUPYOF
      JMP DWRITE
*
TEST4 CMPB CMDCRY
      BNE TEST5
      JSR XOFFST
      STA CORYOF
      JMP DWRITE
*
TEST5 CMPB CMDTST
      BNE DWRITE
*
****                ENTER TEST MODE
*
*
      CLRB
TLOOP LDA #20
TOP   LDX #$C000
WLOOP STB ,X+
      CMPX #$D7FF
      BMI WLOOP
      DECA
      BPL TOP
      INCB
      LDA PIOCMD
      BMI TLOOP
*
*
      JMP BEGIN
*
*
*
*
*
```

```
*
*
*
*
*
*       COMPUTE OFFSET
*
*
*
*

LDA PUPXOF   SET UP FOR ADD LATER
        CLR TEMP2
        STA TEMP3
        LDA ROWSIZ
        LDB PUPYOF
        BMI SWITCH
        MUL          !FUNCTION OFFSET = X + (Y*ROWSIZ)
        ADDD TEMP2    THIS IS PUPXOF IN 16-BIT FORM
        BRA STRIT
SWITCH           NEGB
        INCB
        MUL          !FUNCTION OFFSET = X + (Y*ROWSIZ)
        STD TEMP1
        LDD TEMP2    THIS IS 16-BIT PUPXOF
        SUBD TEMP1
STRIT   STD POFF
*
*
*
*       COMPUTE OFFSET FOR CORNEA
        LDA CORXOF   SET UP FOR ADD LATER
        CLR TEMP2
        STA TEMP3
        LDA ROWSIZ
        LDB CORYOF
        BMI SWCH1
        MUL          !FUNCTION OFFSET = X + (Y*ROWSIZ)
        ADDD TEMP2   CORXOF IN 16-BIT FORM
        BRA STR1
SWCH1   NEGB
        INCB
        MUL          !FUNCTION OFFSET = X + (Y*ROWSIZ)
        STD TEMP1
        LDD TEMP2    CORXOF IN 16-BIT FORM
        SUBD TEMP1
STR1    STD COFF
*
*
******  FIRST DO CLEAR AND THEN WRITE
*
*
*
*

STD TABEND
WLOOP1  LDD ,X++
        ADDD OPOFF
        TFR D,Y
```

```
        LDD #$FFFF
        SYNC
        STD ,Y              DO THE WRITE
        LEAX 2,X            PASS OVER DATA IN ARRAY
        CMPX TABEND
        BNE WLOOP1
*
*
*
*

LDD #CORPTN
        TFR D,X
        ADDD CORSIZ
        STD TABEND
WLOOP2  LDD ,X++
        ADDD OCOFF
        TFR D,Y
        LDD #$FFFF
        SYNC
        STD ,Y              DO THE WRITE
        LEAX 2,X
        CMPX TABEND
        BNE WLOOP2
*
*
*
*
*       WRITE PUPIL AND THEN CORNEA
*
        LDD #PUPPTN
        TFR D,X
        ADDD PUPSIZ
        STD TABEND
*                           SYNC UP WITH THE FS SIGNAL
WLOOP3  LDD ,X++
        ADDD POFF
        TFR D,Y
        LDD ,X++
        SYNC
        STB ,Y              DO THE WRITE
        CMPX TABEND
        BNE WLOOP3
        ADDD COFF
        TFR D,Y
        LDD ,X++
        SYNC
        STB ,Y              DO THE WRITE
        CMPX TABEND
        BNE WLOOP4
*
*
*       HOPEFULLY, 2.03 MS HAVENT ELASPED
*
*
*       GO BACK UP AND LOOK FOR SOMETHING TO DO
*
*
```

```
*
*
*
*
*
        JMP ALOOP
*
IMSG    FCC 'ENTERING TEST MODE'
        FCB $04
MSG1    FCC 'PUPIL/CORNEAL SIMULATION'
        FCB $04
*       INTERUPT ROUTINE
*
*
*
IRQRTN          RTI             DUMMY ROUTINE USED TO SYNC UP TO
THE FS SIGNAL
*
*
*
*
*****   SUBROUTINE DEFINITIONS
*
*
*
XOFFST  LDA PIOCNT
        ASRA            DIVIDE BY 2
        RTS
*
*****   ROM CONSTANTS
*
*
CORPTN  FDB $CBCE       CORNEA PATTERN ADDRESSES AND DATA
        FDB $5555
        FDB $CBED
        FDB $5555
        FDB $CBEE
        FDB $5555
        FDB $CBEF
        FDB $5555
        FDB $CC0E
        FDB $5555
PUPPTN  FDB $CB8D       PUPIL PATTERN ADDRESSES AND DATA
        FDB $0000
        FDB $CB8E
        FDB $0000
        FDB $CB8F
        FDB $0000
        FDB $CBAC
        FDB $0000
        FDB $CBAD
        FDB $0000
        FDB $CBAE
        FDB $0000
        FDB $CBAF
        FDB $0000
        FDB $CBB0
```

```
        FDB  $0000
        FDB  $CBCB
        FDB  $0000
        FDB  $CBCC
        FDB  $0000
        FDB  $CBCD
        FDB  $0000
        FDB  $CBCE
        FDB  $0000
        FDB  $CBCF
        FDB  $0000
        FDB  $CBD0
        FDB  $0000
        FDB  $CBD1
        FDB  $0000
        FDB  $CBEA
        FDB  $0000
        FDB  $CBEB
        FDB  $0000
        FDB  $CBEC
        FDB  $0000
        FDB  $0000
        FDB  $CBF1
        FDB  $0000
        FDB  $CBF2
        FDB  $0000
        FDB  $CC0B
        FDB  $0000
        FDB  $CC0C
        FDB  $0000
        FDB  $CC0D
        FDB  $0000
        FDB  $CC0E
        FDB  $0000
        FDB  $CC0F
        FDB  $0000
        FDB  $CC10
        FDB  $0000
        FDB  $CC11
        FDB  $0000
        FDB  $CC2C
        FDB  $0000
        FDB  $CC2D
        FDB  $0000
        FDB  $CC2E
        FDB  $0000
        FDB  $CC2F
        FDB  $0000
        FDB  $CC30
        FDB  $0000
        FDB  $CC4D
        FDB  $0000
        FDB  $CC4E
        FDB  $0000
        FDB  $CC4F
        FDB  $0000
PUPSIZ          FDB  200          PUPIL SIZE IN BYTES(SIZE OF PUPPIX)
```

```
CORSIZ      FDB 20         CORNEA SIZE IN BYTES(SIZE OF CORPTN)
CMDPPX      FCB $81        COMMAND THROUGH PIO TO CHANGE X PUPIL
CMDPPY      FCB $82        COMMAND THROUGH PIO TO CHANGE Y PUPIL
CMDCRX      FCB $83        COMMAND TO CHANGE X CORNEA
CMDCRY      FCB $84        COMMAND TO CHANGE Y CORNEA
CMDTST      FCB $85        COMMAND TO ENTER TEST MODE
ROWSIZ      FCB $20                    SIZE IN BYTES OF EACH VIDEO ROW
*
*
*

TEMP1   RMB 2           TEMPORARY STORAGE
TEMP2   RMB 1
TEMP3   RMB 1       TEMP2 AND TEMP3 USED FOR 16-BIT STUFF
OLDCMD  RMB 1   PREVIOUS COMMAND
COFF    RMB 2              ADDRESS OFFSET FOR CORNEA
POFF    RMB 2              ADDRESS OFFSET FOR PUPIL
OPOFF   RMB 2       OLD POFF
OCOFF   RMB 2       OLD COFF
TABLND  RMB 2                   ADDRESS OF TABLE END
PUPXOF  RMB 1                   PUPIL OFFSET IN X(HORIZONTAL)
PUPYOF  RMB 1                   PUPIL OFFSET IN Y(VERTICAL)
CORXOF  RMB 1                   CORNEA OFFSET
CORYOF  RMB 1                   CORNEA OFFSET
OLDPX   RMB 1       OLD PUPIL X OFFSET
OLDPY   RMB 1       OLD PUPIL Y OFFSET
OLDCX   RMB 1       OLD CORNEA X OFFSET
OLDCY   RMB 1       OLD CORNEA Y OFFSET
*
    END

END OF PROGRAM
:
```

I claim:

1. Signal sourcing apparatus for actuating an eye tracking oculometer system, said apparatus comprising the combination of:
   means for generating a first sequence of electrical signals representative of an artificial optical background area;
   means for generating a second sequence of electrical signals representative of an artificial first optical image disposed on said background area;
   means for generating a third sequence of electrical signals representative of an artificial second optical image disposable on either said first optical image or on said background area;
   memory means including a plurality of memory elements, means for addressing said memory elements, and means for writing in said memory elements, for storing said first, second, and third sequence electrical signals;
   means for reading said first, second, and third sequence of stored electrical signals in predetermined arrangement from said memory elements and for generating a composite video signal therefrom; and
   means for conveying said composite video signal to a data input port of said oculometer system.

2. The apparatus of claim 1 wherein said first optical image is characteristic of an infrared reflection from a human eye retina.

3. The apparatus of claim 2 wherein said second optical image is smaller than said first optical image and is characteristic of an infrared reflection from an external surface portion of a human eye.

4. The apparatus of claim 3 wherein said second optical image is disposed within the perimeter of said first optical image 5. The apparatus of claim 1 wherein said means for writing includes means for changing the writing order among said memory elements and generating apparent movement of said first and second images with respect to said optical background area.

6. The apparatus of claim 5 wherein said means for reading includes a video processor circuit, a data communication path between said video processor circuit and said memory elements and controlling means for limiting the accessing of said memory elements to one of said means for writing and said means for reading video processor circuit.

7. The apparatus of claim 1 wherein said oculometer data input port is a video camera output signal receiving port of said oculometer system.

8. The apparatus of claim 1 Wherein said three means for generating said memory means, and said means for reading are comprised of a programmed microprocessor.

9. The apparatus of claim 1 further including means for generating a fourth sequence of electrical signals representative of a noise interference signal modulation of said first, second and third signals.

10. The method for testing operation of an eye tracking oculometer system comprising the steps of:
generating a predetermined sequence of electrical signals representing a simulated optical image resident on an optical background;
storing said sequence of signals in an array of memory elements;
reading said stored signals in predetermined order and rate sequence, generating thereby a video signal representative of a position and velocity determined test optical pattern;
substituting said video signal for an optical camera originated video signal in said oculometer system;
measuring the response of said oculometer system against an expected response to said predetermined signals.

11. The method of claim 10 wherein said generating of electrical signals further includes executing a plurality of program instructions in a microprocessor.

12. The method of claim 10 wherein said generating and storing of signals are variable to achieve position, velocity and movement direction variations in said optical pattern.

13. The method of claim 10 wherein said optical pattern includes two images, a first larger image representative of eye retinal reflection and a second smaller image representative of eye corneal reflection.

14. The method of claim 13 wherein said two images are superimposed but movable with respect to each other and with respect to an optical background image.

15. The method of claim 10 wherein said electrical signals are binary signals.

16. Stimulus sourcing apparatus for exercising the functional operation of an eye tracking oculometer system, said apparatus comprising the combination of:
electrical circuit means for generating a first array of electrical signals emulating the human eye retina reflection optical image electrical signals generated in said oculometer;
electrical circuit means for generating a second array or electrical signals emulating the human eye cornea reflection optical image electrical signals generated in said oculometer;
electrical means for generating simulated predetermined positional movement of said first and second optical image electrical signals with respect to a background field and with respect to each other;
means for storing said first and second arrays of electrical signals;
means for coupling said electrical signals between said means for storing and an optical image electrical signal input port of said oculometer system.

17. The apparatus of claim 16 further including means for generating static and dynamic noise signal modulations of said electrical signals.

18. The apparatus of claim 17 wherein said means for storing includes a pixel by pixel organized electronic memory array, and wherein said apparatus further includes a graphics formatting electrical circuit and a computer central processing unit and wherein said computer central processing unit and said graphics formatting electrical circuit are each connected with said pixel by pixel organized electronic memory array in tim shared access thereto.

19. The apparatus of claim 18 wherein said means for generating simulated predetermined positional movement of said optical images includes means for reading said optical image electrical signals in predetermined rate and pattern variation to simulate image position change and movement velocity.

20. The apparatus of claim 19 wherein said oculometer system includes an optical signal to electrical signal transducer device electively connected to said electrical signal input port.

21. The apparatus of claim 17 wherein said first and second array electrical circuit means additionally include means for generating human eye pupil abnormality emulating and cornea abnormality emulating electrical signals.

* * * * *

UNITED STATES PATENT AND TRADEMARK OFFICE
CERTIFICATE OF CORRECTION

PATENT NO. : 4,798,214

DATED : January 17, 1989

INVENTOR(S) : Michael W. Haas

It is certified that error appears in the above-identified patent and that said Letters Patent is hereby corrected as shown below:

Col 1, line 67, "noise also" should read ---noise, also---.

Col 3, line 31, "o.f" should read ---of---.

Col 5, line 24, "oculometer it" should read
      ---oculometer, it---.

Col 5, line 26, replace "-a signal" with ---and---.

Col 5, line 27, replace "and" with --- -a signal---.

Col 5, line 56, "block 150" should read ---block 150.---.

Col 8, line 31, "o" should read ---or---.

Col 8, line 34, "70" should read ---704---.

Col 8, line 35, "70" should read ---708---.

Col 8, line 43, a comma should follow "provide".

Col 9, line 7, "path. a" should read ---path, a---.

Col 10, line 10, a period should follow "syncronization".

Col 10, line 25, "blocks 150" should read ---blocks 150,---.

Col 10, line 37, "Way" should read ---way---.

Col 12, line 21, "o" should read ---of---.

Col 13, line 12, "milisecond" should read ---millisecond---.

Col 15, line 26, before "INIT1 LEAX IRQRTN,PCR" insert lines
    ---IFNE MNTRLD
        FDB $2OFE---.

Col 17, line 19, delete "*".

UNITED STATES PATENT AND TRADEMARK OFFICE
CERTIFICATE OF CORRECTION

PATENT NO. : 4,798,214

DATED : January 17, 1989

INVENTOR(S) : Michael W. Haas

It is certified that error appears in the above-identified patent and that said Letters Patent is hereby corrected as shown below:

```
Col 17, line 20, before "TEST3 CMPB CMDPPY" insert lines
---TEST2 CMPB CMDCRX
         BNE TEST3
         JSR XOFFST
         STA CORXOF
         JMP DWRITE
      *---.

Col 19, lines 9-16, "*" should read
*           FOUND NEW OFFSETS AND STORED THEM
*           NOW WRITE OUT THE PUPIL AND THEN CORNEA
*
DWRITE        LDD POFF
    STD OPOFF
    LDD COFF
    STD OCOFF    SAVE OLD POINTERS
*

Col 21, line 43, before "ADDD COFF" insert lines
---*
   *
   *
   *
         LDD #CORPTN
         TFR D,X
         ADDD CORSIZ
         STD TABEND
   WLOOP4 LDD ,X++---.

Col 25, line 22, before "FDB $0000" insert lines
---FDB $CBED
   FDB $0000
   FDB $CBEE---.
```

UNITED STATES PATENT AND TRADEMARK OFFICE
CERTIFICATE OF CORRECTION

PATENT NO. : 4,798,214

DATED : January 17, 1989

INVENTOR(S) : Michael W. Haas

It is certified that error appears in the above-identified patent and that said Letters Patent is hereby corrected as shown below:

```
Col 27, line 11, "*" should read
        ORG $D800
*       RAM
*       CONSTANTS
*
*
```

Col 28, claim 4, line 3, "image" should read ---image.---.

Col 30, claim 18, line 8, "tim" should read ---time---.

Signed and Sealed this

Tenth Day of March, 1992

Attest:

HARRY F. MANBECK, JR.

*Attesting Officer*       *Commissioner of Patents and Trademarks*